United States Patent [19]
Kuster et al.

[11] Patent Number: 5,681,530
[45] Date of Patent: Oct. 28, 1997

[54] TRANSPORT SYSTEM FOR FLUID ANALYSIS INSTRUMENT

[75] Inventors: Martin Kuster, Eschenbach; Marco Forster, Grueningen, both of Switzerland

[73] Assignee: Ortho Diagnostic Systems Inc., Raritan, N.J.

[21] Appl. No.: 75,028

[22] Filed: Jun. 11, 1993

[51] Int. Cl.⁶ .................................................. G01N 35/02
[52] U.S. Cl. .......................... 422/63; 422/64; 422/72; 422/100; 436/43; 436/45; 436/47; 436/48; 436/177; 436/180
[58] Field of Search .................. 422/63–67, 72, 422/68.1, 104, 100; 435/808, 809; 436/43, 45, 47, 48, 49, 54, 165, 174, 177, 180

[56] References Cited

U.S. PATENT DOCUMENTS

| | | | |
|---|---|---|---|
| Re. 29,725 | 8/1978 | Johnson et al. | 23/280 R |
| 3,691,017 | 9/1972 | Brown et al. | 195/103.5 R |
| 4,038,030 | 7/1977 | Albright et al. | 23/230 R |
| 4,058,367 | 11/1977 | Gilford | 422/63 |
| 4,104,031 | 8/1978 | Robuchon-Merovak et al. . | |
| 4,197,088 | 4/1980 | Meserol et al. . | |
| 4,400,353 | 8/1983 | Meserol et al. . | |
| 4,457,893 | 7/1984 | Takekawa . | |
| 4,503,011 | 3/1985 | Hubeau . | |
| 4,558,946 | 12/1985 | Galle et al. . | |
| 4,575,492 | 3/1986 | David et al. . | |
| 4,580,895 | 4/1986 | Patel . | |
| 4,678,752 | 7/1987 | Thorne et al. | 435/291 |
| 4,683,120 | 7/1987 | Meserol et al. . | |
| 4,727,033 | 2/1988 | Hijikata et al. . | |
| 4,767,600 | 8/1988 | Vicario . | |
| 4,861,554 | 8/1989 | Sakuma . | |
| 4,873,633 | 10/1989 | Mezei et al. . | |
| 5,158,895 | 10/1992 | Ashihara et al. | 436/256 |
| 5,232,665 | 8/1993 | Burkovich et al. | 422/65 |
| 5,260,872 | 11/1993 | Copeland et al. | 364/413.07 |

*Primary Examiner*—James C. Housel
*Assistant Examiner*—Long V. Le

[57] ABSTRACT

A transport system for instruments utilized in the analysis of fluids and, more particularly, a transport system which is adapted to be employed in the automated analysis of blood samples. The transport system including cassette transporting and filling structure is provided to extend over and operatively interconnect various stations of a blood analysis apparatus consisting of a blood sample and reagent supply holder, a storage unit for empty cassettes, a carousel or rotor containing an incubator chamber and a chamber at room-temperature for the receipt and filling with blood samples of cassettes, a centrifuge and an automated optical readout rotor.

14 Claims, 3 Drawing Sheets

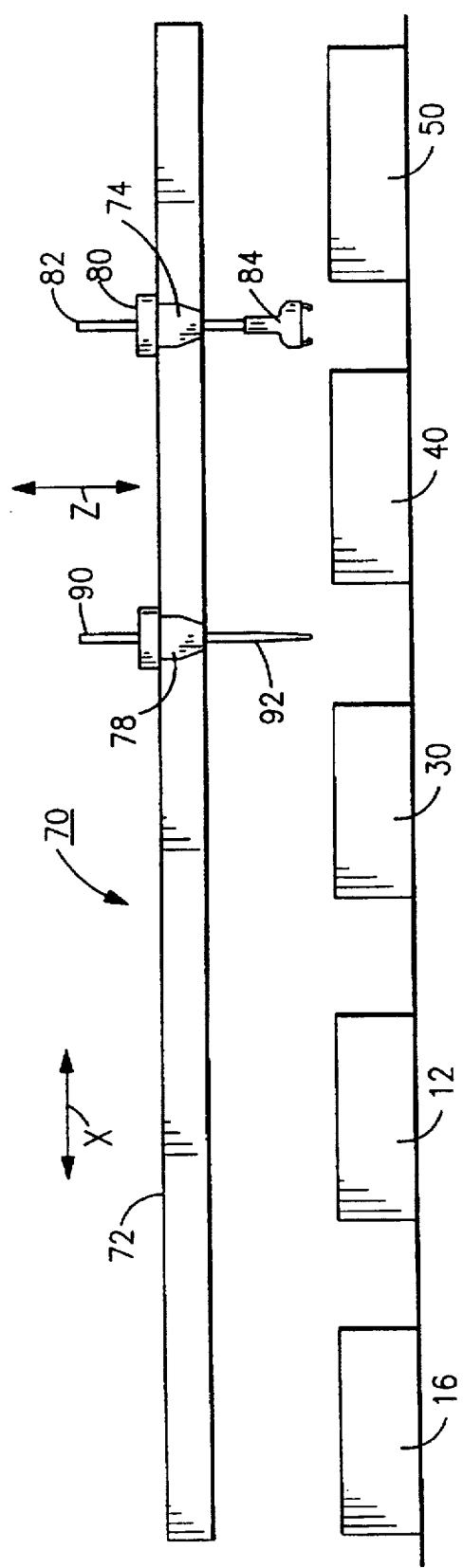
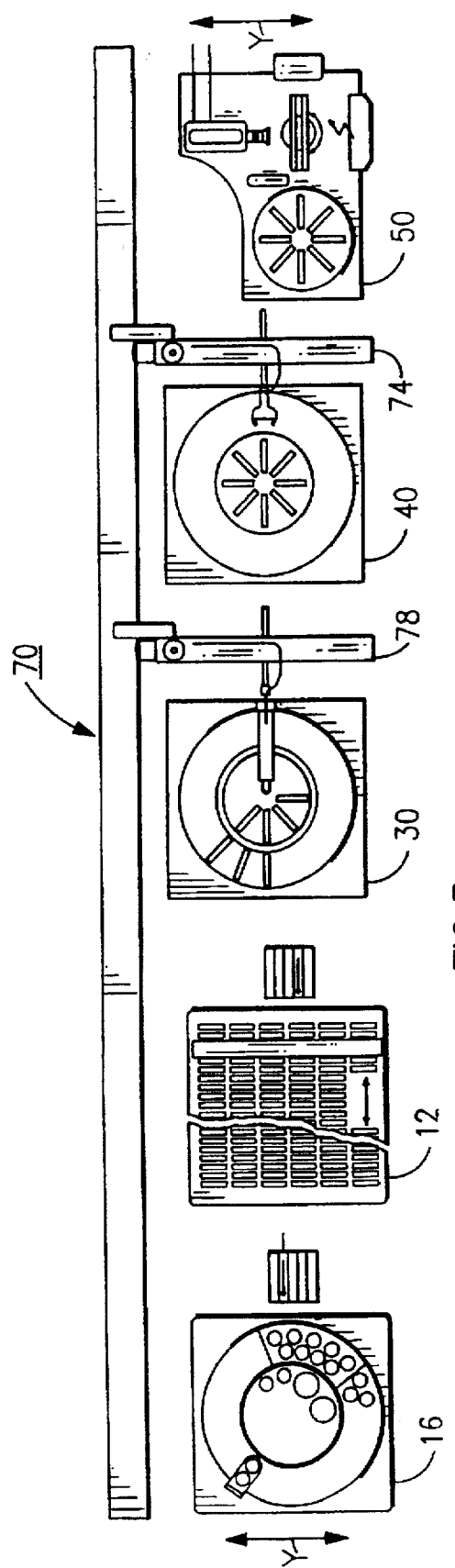
FIG.2
FIG.3

TRANSPORT SYSTEM FOR FLUID ANALYSIS INSTRUMENT

BACKGROUND OF THE INVENTION

Field of the Invention

The present invention relates to a transport system for instruments utilized in the analysis of fluids and, more particularly, relates to a transport system adapted to be employed in the automated analysis of blood samples.

In the analysis of fluids, for instance, such as blood samples and the like, it has become important to be able to implement a procedure in which the samples are rapidly prepared in an essentially automated mode for analysis with a minimal need for manual intervention or handling, and wherein such blood samples are transported in a computer-controlled manner from an initial preparation station to a final auto-read station providing for the analysis of the prepared blood sample or samples. To achieve the foregoing, provision may be made for the storage of cassettes transportable to a suitable carousel which may incorporate an incubator rotor and a rotor for operating at room temperature; wherein a pipettor is adapted to aspirate fluids comprising blood samples and specified selected reagents and to transport these fluids to the cassette or cassettes stored in the carousel and fill them into wells in the cassettes pursuant to the particular blood analyses which are to be implemented. Thereafter, the cassette or cassettes containing the blood and reagent samples is or are transported to a centrifuge where the samples are centrifuged to provide for appropriate mixing thereof, and are then transported to a further carousel or rotor operatively associated with an auto-reader for effectuating the spectrographic or visual analysis of the blood sample. When the analysis of the blood sample is considered to be qualitatively satisfactory, there is then carried out the discarding of the cassette.

SUMMARY OF THE INVENTION

In order to be able to implement the foregoing sequence in a substantially automated manner, a transport system including cassette transporting and filling structure is provided to extend over and operatively interconnect various stations of a blood analysis apparatus consisting of a blood sample and reagent supply holder, a storage unit for unused cassettes, a carousel or rotor containing an incubator chamber and a room temperature chamber for the receipt and filling with blood samples of cassettes, a centrifuge and an automated readout rotor. The essentially computer-controlled operation of the transport system and instruments employed which enables movements of the various operative components in at least three mutually orthogonal directions; in effect, within mutually perpendicular horizontal planes and in a vertical direction, facilitates a cassette, and preferably a plurality of cassettes each having a plurality of blood sample and reagent-receiving wells formed therein, to be transported to and suitably positioned in the carousel containing the room temperature and the incubator rotors, and with the respective wells of each cassette being fillable, subsequent to piercing of the protective foil thereon, with suitable quantities of fluid which is to be analyzed, such as blood combined with specific reagents in correlation with the intended type of blood test, and, subsequent to either suitable heat treatment in the carousel containing the incubator rotor or merely filled in the rotor at room temperature, transported by means of the transport system to a centrifuge for centrifuging for a predetermined period of time at specified rates of rotational speeds. Thereupon, the centrifuged cassettes and their contents are transported to a further carousel or rotor containing positions for receiving the centrifuged cassettes, which are adapted to be indexed into operative alignment with an auto-reader for optical analysis of the contents of the cassettes, and thereafter discarded upon recordal of the data derived therefrom.

The transport system incorporates a plurality of mutually displaceable horizontal beams of which a first horizontal stationary beam extends along the length of the apparatus containing the stations for implementing the various blood preparation and analyses; with two horizontal beams extending normal, to the first beam being displaceable along the axial length of the first beam, with such other beams being equipped with, respectively, a gripper for clampingly engaging and transporting cassettes, and with a pipettor for selectively supplying the cassettes with blood samples and reagents. Hereby, the gripper and the pipettes are mounted so as to be displaceable along the axial lengths of the respective beams on which they are mounted as well as being vertically movable so as to be movable into either inoperative or operative positions, as elucidated hereinbelow.

The foregoing procedure in utilizing the inventive transport system may be implemented in a fully automated and computer-controlled mode in which one or more cassettes each having one or more wells filled with fluid or blood samples and reagents and instruments for that purpose are transported to the various stations and samples treated for analysis of the contents thereof.

Accordingly, it is an object of the present invention to provide a transport system for fluid analysis instruments.

Another object of the present invention is to provide a transport system of the type described enabling the analysis of one or more samples of a fluid, such as blood, in conjunction with the automated preparation of the samples at various stations prior to analysis.

Still another object of the present invention is to provide a transport system including a plurality of orthogonally displaceable transport components automatedly movable between stations of the apparatus, including a gripper structure for engaging and transporting cassettes, and independently pipettor structure for supplying the cassette or cassettes with suitable blood samples and reagents for their analysis.

BRIEF DESCRIPTION OF THE DRAWINGS

Reference may now be had to the following detailed description of an exemplary embodiment of a transport system for blood analysis instrumentation, taken in conjunction with the accompanying drawings; in which:

FIG. 2 illustrates a front elevational view of a transport system for blood analysis instruments constructed pursuant to the invention;

FIG. 3 illustrates a top plan view of the transport system of FIG. 2;

DETAILED DESCRIPTION OF A PREFERRED EMBODIMENT

Figure 1:
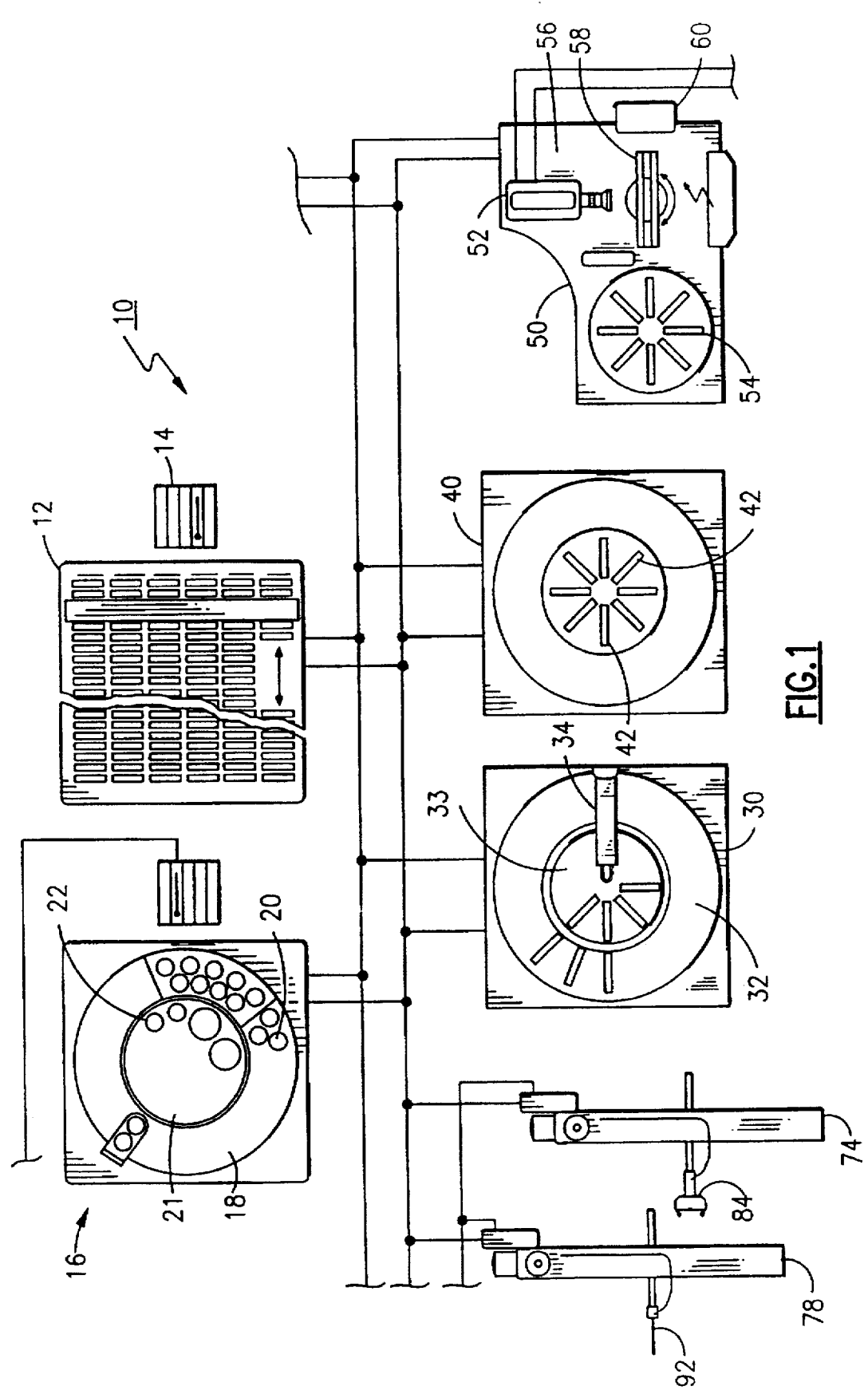
FIG. 1 illustrates a generally diagrammatic representation of an arrangement for effectuating blood analyses.

Reverting now in greater particularity to the drawings, and especially the diagrammatic representation of FIG. 1, there is generally disclosed an apparatus 10 for implementing the analysis of blood samples from one or more patients, and wherein the apparatus 10 is adapted to be utilized in conjunction with a transport system for a blood analysis instrument constructed pursuant to the invention, as described in detail hereinbelow. Apparatus 10 is described in greater detail in copending application Ser. No. 08/193,997, for "An Automated Blood Analysis System," filed herewith, the disclosure of which is herein incorporated by reference.

The blood analysis apparatus 10 includes a work surface supporting in a generally linear array a plurality of operating unit of the apparatus. These include cassette storage unit 12 adapted to store a plurality of unused cassettes, of the type as are illustrated in FIGS. 5 through 8 of the drawings, in a generally upright position. Located proximate the cassette storage unit 12 is a suitable bar code reader 14 for reading information on the cassettes and recording the information in a suitable computer memory storage.

A blood sample and reagent rotor 16 is equipped with an annular space 18 for the containment of a plurality of blood samples in vials 20, with such samples having been obtained from one or more patients, whereas a further circular space 21, such as a central space in the rotor 16, is adapted to house vials 22 of differing kinds of reagents which are adapted to be selectively mixed with various of the blood samples in accordance with the types of analyses which are to be implemented on the blood samples.

Arranged on the work surface is a carousel or rotor 30 including an outer annular region 32 for receiving and housing at room temperature an array of cassettes adapted to be arranged in a generally upright orientation and peripherally spaced to extend spoke-like, with central region 33 also adapted to receive a further similar array of cassettes, wherein the central rotor region is adapted to be heated so as to essentially constitute an incubator. A piercing device 34 is operatively associated with the carousel 30 and is adapted to selectively pierce through a sealing foil located on each cassette, in a manner as described hereinbelow, so as to enable the supplying of fluids, such as blood samples and reagents, to the cassettes in the carousel 30.

A centrifuge unit 40 also includes a plurality of circumferentially spaced and radially extending slots 42 each adapted to respectively receive a cassette from the carousel 30 constituting the incubator and room temperature rotor unit subsequent to the filling of the cassette or cassettes with blood samples and reagents in carousel 30.

Located on the work surface in line with the centrifuge unit 40 is a further rotor or carousel 50 having an auto-reader 52 operatively associated therewith. The rotor 50 is adapted to receive in suitable receiving slots 54 a plurality of upright oriented, circumferentially spaced and radially extending cassettes from the centrifuge unit 40, with such auto-reader 52 being operatively connected with a device 56 for optically reading and analyzing the contents, i.e. the blood/reagent fluid, of cassettes conveyed thereto from the rotor 50, and including means for transmitting the information concerning the results of the analysis to a computer and/or video monitor (not shown). Connected to a discharge slot 58 of the auto-reader 52 is a waste disposal 60 adapted to receive cassettes subsequent to the completion of satisfactorily acceptable analysis data of the contents from the auto-reader.

In order to facilitate the automated and computer-controlled analysis of various fluid or blood samples, as shown in FIGS. 2 and 3 of the drawings extending elevated above and along the extent of the units 12, 16, 30, 40 and 50 of the apparatus 10 as described with regard to FIG. 1, is a transport system 60 consisting of a plurality of operatively interconnected components which are mutually displaceable relative to each other in three orthogonal directions; in effect, in two horizontally-oriented transverse or perpendicular directions, such as axes X and Y, and in vertical up and down directions, such as axis Z; in essence, along the X, Y and Z axes.

The transport system 70 includes a first horizontally-extending stationary beam structure 72 longitudinally above the edge of the various units 12, 16, 30, 40 and 50 which are arranged in a generally linear array on the work surface, or similar suitable supporting surface. A first beam-shaped horizontal arm 74 extends normally of the beam 72 across the units, and has one end attached to a drive arrangement on beam 72 so as to be displaceable the length of beam 72 is both directions thereof along axis X.

A second similar horizontal beam-shaped arm 78 also extends normal of beam 72, and has one end attached thereto so as to be displaceable over the length of beam 72 along axis X; in essence, extends in parallel with the arm 74, but at variable distances therewith during operation of system 70.

Mounted to the arm 74, as clearly shown in FIG. 2, is a movable unit 80 which includes a vertically displaceable toothed rack 82, the lower end of which has a gripper member 84 attached thereto, upwardly and downwardly displaceable along axis Z and whereby the unit 80 is selectively movable along the length of arm 74 in both directions of arrow Y.

Similarly, mounted on the beam-shaped arm 78 is a unit 90 vertically displaceable along the direction of arrow Z, and which is also horizontally movable along the longitudinal extent of the beam 78 along the direction of arrow Y. The unit 90 incorporates a pipettor 92 which is adapted to aspirate and dispense fluids in a manner which is well known in the technology.

In essence, due to the displaceability of the beams 74 and 78 along the directions of axis X defined by beam structure 72; the movability of the gripper unit 80 along beam 74 and its vertical shiftability along axis Z; and similarly the displaceability of the pipettor 92 along its beam arm 78 in the direction of axis Y, and its concurrent ability to be vertically shifted along the direction of axis Z, the transport system 40 provides for a three-dimensional or orthogonal movability in the functioning thereof.

The above-mentioned components 74, 78, 80 and 90 are all selectively placed into motion in various directions and at differing periods of time as required by the operation of the transport system 70 through suitable computer-controlled driving elements which are associated with the respective operating units of the transport system.

As illustrated in FIGS. 5 through 8, each cassette 100 which is adapted to be employed for the analysis of blood samples is basically constituted from a transparent or translucent thermoplastic material.

Figure 6:
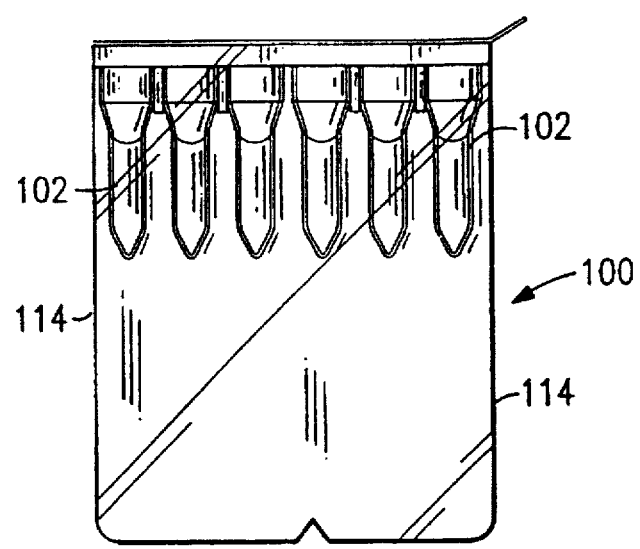
FIGS. 6, 7 and 8 illustrate, respectively, front, end and top plan views of the cassette of FIG. 5.
Figure 7:
Figure 8:
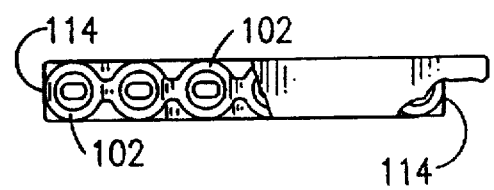

The cassette 100 has an essentially rectangular configuration, as shown in FIG. 6, and is of a decreasing cross-sectional thickness from the upper end towards the bottom thereof. The cassette 100 may incorporate six wells 102 for receiving blood samples, although fewer or larger amount of wells may be formed in each cassette. The transparency of the plastic material of the cassette enables any contents of the wells to be optically examined and analyzed. The upper opening of each well 102 is sealed by means of a liquid-impervious foil 104 which covers and is adhesively fastened to the upper surface of the cassette 100 and which maintains the interior of each well 102 in a clean condition.

The openings or slots in the storage unit 12 for receiving and storing the cassettes 100, are adapted to maintain the cassettes in an upright condition, as illustrated herein.

Figure 4:
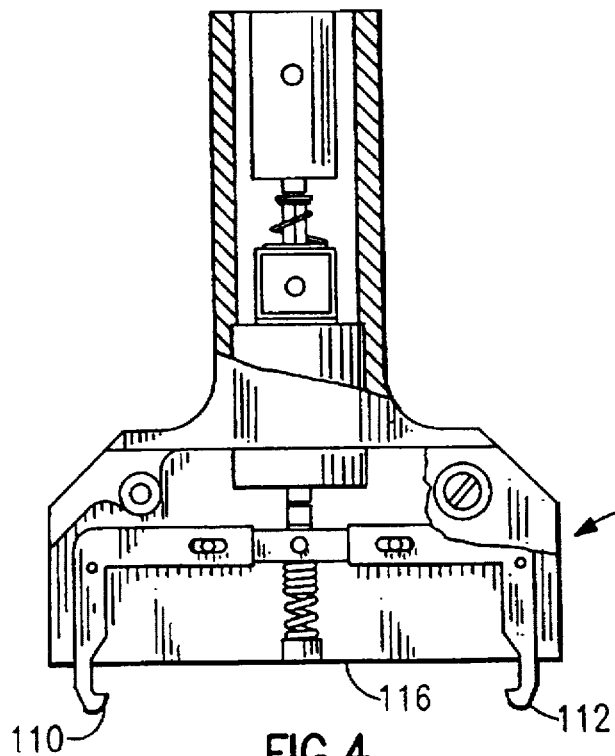
FIG. 4 illustrates, on an enlarged scale, a schematic view of a gripper for cassettes employed for the containment of blood samples which are to be analyzed, utilized in the inventive transport system.
Figure 5:
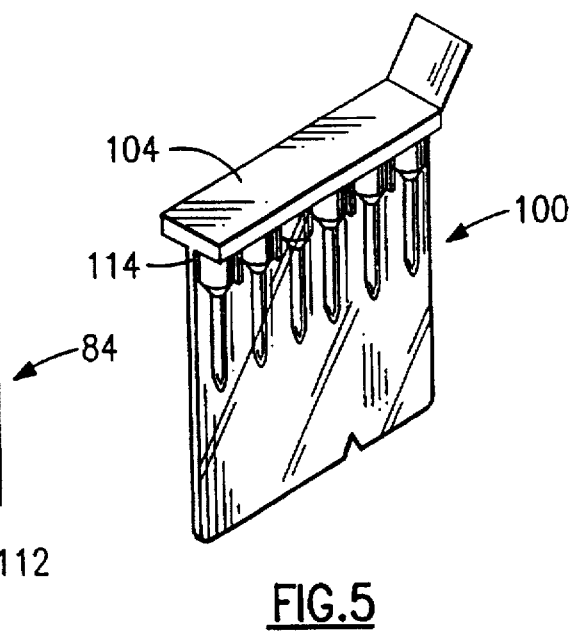
FIG. 5 illustrates a perspective view of a cassette for blood samples employed in conjunction with the transport system.

The gripper member 84 of unit 80, as shown schematically in the enlarged detail of FIG. 4 of the drawings, includes clamping end members 110 and 112 which, under spring-loaded and program-controlled actuation, are adapted to spread apart so as to slide over the end surfaces 114 of the cassette 100 and are closeable so as to clampingly engage the opposite ends of the cassette during lifting and transporting of cassette 100 by the gripper unit 80.

OPERATION OF THE TRANSPORT SYSTEM

In operation, describing the transport and analysis of a single cassette, the transport system 70 functions essentially as follows:

A cassette 100 stored in storage unit 12 is moved into a dispensing condition below an opening in the unit, and the arm 74 is moved along beam structure 72 until it is superimposed over the opening in the storage unit and the gripper unit 80 moves in the direction of axis Y along arm 74 until superimposed over the cassette 100 which is to be removed from the storage unit 12. Thereafter, the toothed rack 82 supporting the gripper member 84 at its lower end is lowered with the gripper clamping end members 110, 112 being maintained in a spread apart condition until the lower surface 116 of the gripper member 84 between end members 110, 112 contacts the upper surface of the cassette 100, and with the end surfaces 114 thereof then being clampingly engaged by gripper end members 110, 112. Thereafter, the cassette 100 is lifted outwardly of the unit 12 and passed adjacent bar code reader 14 which will ascertain information as to the proper orientation of the cassette, that the desired cassette has been removed from the storage unit 12, that the cassette has not reached its expiration dating, and miscellaneous information as to the sequence number and lot number of the cassette, all of which information may then be transmitted to the memory of a computer and stored therein.

Upon the foregoing information indicating that the cassette 100 which has been withdrawn from the storage unit 12 is acceptable, the arm 74 with the gripper member 84 clamping the cassette 100 is transported along beam structure 72 in the direction of arrow X until the arm 74 is positioned above the carousel 30 containing the central incubator area 33 and annular outer area 32 in which cassettes 100 are to be stored at room temperature, depending upon the kind of heating treatment which is to be imparted to the contents of the cassette 100.

Upon the positioning of the cassette 100 in the desired carousel area 32 or 33, and release and withdrawal of gripper member 84, a piercer (not shown in detail) punches one or more apertures through the foil 104 to provide access to one or more of the wells 102 depending upon the number of analyses which are to be implemented to the various blood samples.

Thereafter, the arm 74 with the gripper member 84 raised is moved in the direction of axis X towards the right along beam structure 72, in effect, in a direction away from the rotor 16 containing the various blood samples and reagents.

At that point in time, the arm 78 supporting the pipettor unit 90 is positioned over the rotor 16 by displacement of the arm 78 along beam 72 in the direction of arrow X, until the arm 78 is located above the blood sample which is to be removed therefrom. Thereupon, the pipettor 92 is moved in the direction of axis Y along arm 78 until positioned directly above the desired blood sample vial, and lowered into the blood so as to aspirate a quantity thereof. Thereafter, the pipettor 92 is raised, and transported towards the right along axis X until superimposed over the previously pierced opening of a well 102, into which the blood sample is then introduced. This procedure is effectuated by displacing the pipettor 92 along the direction Y until superimposed over the pierced aperture in the well 102, lowering the pipettor 92 and allowing the fluid or blood to flow into the well.

Upon completion of the foregoing, the pipettor 92 is raised and the arm 78 again displaced along beam 72 towards the left in axis X, with an interim immersion of the pipettor 92 into a washing unit (not shown), and thereafter the pipettor inserted into a vial containing a suitable reagent which is to be employed for the analysis of the previously aspirated blood sample.

The arm 78 with the pipettor 92 is then again moved as heretofore into position above the carousel 30 until the pierced well 100 is in vertical alignment therewith, the pipettor lowered and the reagent is discharged into the blood sample contained in the well 102.

This procedure may be repeated for any number of wells 102 in the cassette 100, until as many wells are filled with blood samples and various reagents as required to implement analyses thereon.

After completion of the foregoing sequences of operation by the pipettor 92, the latter is again moved with its arm 78 towards the left along axis X and permitted to remain in an idle or inoperative position.

Thereafter, the arm 74 mounting the unit 80 with the gripper is moved over the cassette in the carousel 30 and, if the latter is located in the area 32 thereof for storage at room temperature, and the cassette contents do not require incubation, the cassette is gripped by the clamping ends 110, 112 of the gripper member 84 and raised upwardly for transport to centrifuge unit 40. Alternatively, in the event that the blood sample and reagent in the cassette 100 require incubation, whereby the cassette has been stored in the central incubator part 33 of the carousel unit 30, the cassette contents are incubated; for example, for ten minutes at 37° C., and thereafter gripped by the gripper member 84 and transported to the centrifuge unit 40 analogous to the manner in which the cassette was previously introduced into the carousel 30.

Subsequent to insertion of the cassette 100 into centrifuge 40, the centrifuge spins; for instance, initially for two minutes at 55g and for three minutes at 199g, so as to provide for suitable admixing of the blood sample and reagent in each of the respective wells. In the event that only a single cassette is transported into the centrifuge 40, a blank or balancing cassette may be introduced radially oppositely thereof to ensure balancing of the rotor of the centrifuge 26. Upon completion of the centrifuging action, the arm 74 with the gripper member 84 is again positioned over the centrifuged cassette 100, the latter being grippingly engaged by the gripping members 110, 112, and raised upwardly and then transported toward the right to be deposited, in a mode as previously described into a suitable receiving slot 54 provided for the cassette 100 in the rotor or carousel 50 of the auto-reader unit 52.

Thereupon, the carousel 50 is rotated until the cassette 100 comes into alignment with optical reader unit 56, and slid in front of the unit 56 (not described in detail) which will facilitate the optical examination of the contents in the well 102 or wells of the cassette 100 and transmit this information to a suitable computer and/or video screen (not shown). Upon indication that all of the information obtained was satisfactory as recorded relative to the analysis of the contents of each well 102 of the cassette 100, the latter is then expelled by a pusher or the like (not shown) into a suitable waste disposal receptacle 60.

Although the foregoing sequence of operation has been described in connection with the filling and transporting of a single cassette, in which one or more wells 102 may be pierced at the incubator carousel 30, the process may be repeated so as to load the incubator unit 30 with a plurality of cassettes, in which all of the wells 102 of the cassettes may be pierced and then sequentially filled with suitable blood samples (blood cells and/or serum) and various types of reagents as to enable the incubation and/or storage at room temperature of a considerable number of cassettes which are being filled with blood samples, which may then be transported to and fill the centrifuge unit 40, and to facilitate the subsequent filling of the automatic reader rotor 50 with a plurality of blood sample and reagent-filled cassettes 100. This will enable the implementation of a large number of analyses in a rapid and automated computer program-controlled manner.

Upon completion of the foregoing, and while the autoreader rotor 50 is in the process of advancing cassettes to the optical reading unit 56, the previously described transporting and cassette-filling procedure may be continued in the loading of the incubator unit 30 with cassettes and supplying the latter with fluids from the pipettor 92, and then transporting these to the centrifuge 40 so as to always have a supply of processed cassettes available for continual analyses of the cassette contents.

The foregoing is adapted to be computer program-controlled and the movement of the arm 74 mounting the gripper member 84 and the correlation of the functioning therewith of arm 78 mounting the pipettor 92 and their relative movements along beam structure 72, is coordinated so as to provide the most rapidly possible and automated analyses of the cassette contents.

While there has been shown and described what is considered to be a preferred embodiment of the invention, it will, of course, be understood that various modifications and changes in form or detail could readily be made without departing from the spirit of the invention. It is, therefore, intended that the invention by not limited to the exact form and detail herein shown and described, nor to anything less than the whole of the invention herein disclosed as hereinafter claimed.

What is claimed is:

1. A transport system for analysis of fluids contained in at least one cassette having at least one fluid-receiving well, said transport system being functional in orthogonal directions of movement for transporting said at least one cassette between a plurality of work stations and for supplying fluids to be analyzed to said well of said cassette; said transport system comprising:

(a) transporting means extending between said plurality of work stations;

(b) gripping means movably mounted on said transporting means for selectively clampingly engaging a cassette at a first said work station;

(c) gripper transporting means for transporting said gripping means and cassette to a second said work station, said gripping means depositing said cassette at said second work station;

(d) a pipettor operatively mounted on said first-mentioned transporting means, said pipettor being displaceable along said transporting means for successively aspirating specified fluids from a supply source of said fluids, said pipettor being transportable to said second work station to sequentially fill said fluids into said well of said cassette, said pipettor being displaced from said second work station by said transporting means subsequent to filling said well with said fluids;

(e) said gripper transporting means reconveying said gripping means to said second work station for clampingly engaging said fluid-containing cassette and transporting said cassette to a third said work station;

(f) said gripping means releasing said cassette at said third work station for treatment of the fluid contained in said cassette;

(g) said gripping means reengaging said cassette upon completion of a treatment of the fluid contained therein, and said gripper transporting means conveying said gripper means and cassette to a fourth work station and depositing said cassette at said fourth work station to facilitate analysis of the fluid contained in the well of said cassette, wherein said first-mentioned transporting means comprises a first horizontal beam member extending between said work stations; a second horizontal beam member extending normally to said first beam member and having one end attached thereto so as to be movable along the axial length of said first beam member, said gripping means being mounted on said second beam member for axial displacement therealong, and said gripping means is mounted for vertical displacement relative to said second beam member; and a third horizontal beam member extending normally to said first beam member has one end attached thereto so as to be movable along the axial length of said first beam member, said pipettor being mounted on said third beam member for axial displacement therealong, and said pipettor is mounted for vertical displacement relative to said third beam member.

2. A transport system as claimed in claim 1, wherein said second and third beam members are independently movable along said first beam member in parallel adjustably spaced relationship relative to each other.

3. A transport system as claimed in claim 1, wherein said first work station comprises means for storing a plurality of unused of said cassettes, said gripping means selectively engaging successive of said cassettes for sequential conveyance by said transporting means to predetermined cassette depositing locations at said second work station.

4. A transport system as claimed in claim 3, wherein said second work station includes first depositing locations for housing cassettes at substantially room temperature and second depositing locations in an incubator for housing cassettes in an incubating environment adapted to heat said cassettes to predetermined elevated temperatures.

5. A transport system as claimed in claim 3, wherein each said cassette includes a plurality of wells, each of said wells of each cassette being fillable by said pipettor with a specific combination of fluids which are to be analyzed.

6. A transport system as claimed in claim 1, wherein said third work station comprises a centrifuge for centrifuging the fluid contained in said at least one cassette at predetermined rotational speeds.

7. A transport system as claimed in claim 1, wherein said fourth work station comprises means for the optical reading of the fluid in said at least one cassette.

8. A transport system as claimed in claim 1, wherein said fourth work station comprises a carousel for receiving a plurality of said cassettes each having a plurality of fluid-filled wells transported thereto from said third work station by said gripping means being conveyed along said transporting means.

9. A transport system as claimed in claim 8, wherein said carousel includes means for sequentially discarding each said cassette subsequent to implementing an analysis of the fluid contents of each well thereof.

10. A transport system as claimed in claim 1, wherein said fluid which is pipetted into said cassette at said second work station by said pipettor comprises blood samples and a reagent selected in dependence upon specified analysis of the blood sample.

11. A transport system as claimed in claim 10, wherein the at least one fluid filled cassette in the incubator is incubated for a period of 10 minutes at 37° C.

12. A transport system as claimed in claim 6, D wherein said at least one cassette is centrifuged for two minutes at about 55g and thereafter for three minutes at about 199g.

13. A transport system as claimed in claim 1, wherein said gripping means and said pipettor are each movable in three mutually orthogonal directions.

14. A transport system as claimed in claim 13, wherein the movements of said gripper means and of said pipettor are correlated with each other and with the cassette contents pursuant to a computerized program.

* * * * *

UNITED STATES PATENT AND TRADEMARK OFFICE

CERTIFICATE OF CORRECTION

U.S. Patent No.:   5,681,530

Dated:             October 28, 1997

Inventors:         Martin Kuster
                   Marco Forster

It is certified that error appears in the above-identified patent and that said Letters Patent are hereby corrected as shown below:

Column 8, line 23, delete "gripper" and insert therefor --gripping--.

Column 10, line 4, delete "fluid filled" and insert therefore --fluid-filled--.

Column 10, line 6, after 'in claim 6,' delete "D".

Signed and Sealed this

Fifth Day of May, 1998

*Attest:*

BRUCE LEHMAN

*Attesting Officer*      Commissioner of Patents and Trademarks